(12) United States Patent
Schröder

(10) Patent No.: US 10,094,659 B2
(45) Date of Patent: Oct. 9, 2018

(54) METHOD AND APPARATUS FOR DETERMINING PROPERTIES OF A PIPELINE, IN PARTICULAR THE POSITION OF A BRANCH OF A SEWAGE PIPELINE

(71) Applicant: Hochschule Offenburg, Offenburg (DE)

(72) Inventor: Werner Schröder, Offenburg (DE)

(73) Assignee: HOCHSCHULE OFFENBURG, Offenburg (DE)

( * ) Notice: Subject to any disclaimer, the term of this patent is extended or adjusted under 35 U.S.C. 154(b) by 203 days.

(21) Appl. No.: 14/380,131

(22) PCT Filed: Feb. 21, 2013

(86) PCT No.: PCT/DE2013/100067
§ 371 (c)(1),
(2) Date: Nov. 13, 2014

(87) PCT Pub. No.: WO2013/123939
PCT Pub. Date: Aug. 29, 2013

(65) Prior Publication Data
US 2015/0114120 A1    Apr. 30, 2015

(30) Foreign Application Priority Data

Feb. 22, 2012 (DE) .................. 10 2012 101 416

(51) Int. Cl.
*G01N 29/12* (2006.01)
*G01B 17/00* (2006.01)
(Continued)

(52) U.S. Cl.
CPC .............. *G01B 17/00* (2013.01); *G01M 99/00* (2013.01); *G01N 29/07* (2013.01); *G01N 29/12* (2013.01);
(Continued)

(58) Field of Classification Search
CPC ....... G01B 17/00; G01M 99/00; G01N 29/12; G01N 2291/044; G01N 29/07;
(Continued)

(56) References Cited

U.S. PATENT DOCUMENTS

| 3,508,433 A * | 4/1970 | Bustin | F16L 55/28 |
| | | | 73/40.5 A |
| 6,453,566 B1 * | 9/2002 | Bottinelli | B23Q 1/34 |
| | | | 33/1 M |

(Continued)

FOREIGN PATENT DOCUMENTS

| DE | 2414204 C3 | 5/1977 |
| DE | 102009050856 A1 | 4/2011 |

(Continued)

OTHER PUBLICATIONS

German Patent and Trademark Office Action (GPTO Action) dated Feb. 7, 2013 in German priority application Serial No. 10 2012 101 416.7, together with an English translation of a portion of the GPTO Action identifying the relevance of DE 24 14 204 C3.

(Continued)

*Primary Examiner* — Manish S Shah
*Assistant Examiner* — Rose M Miller
(74) *Attorney, Agent, or Firm* — The Culbertson Group, P.C.

(57) ABSTRACT

A method for determining properties of a pipeline includes feeding a sound wave signal at a predetermined feed point into the pipeline so that the sound wave signal propagates in an axial direction of the pipeline. The frequency spectrum of the transmitted sound wave signal has a frequency component or a spectral range with a maximum frequency that is smaller than the lower limit frequency for the first upper mode. Reflected portions of the transmitted sound wave signal are detected as received sound wave signal and are (Continued)

evaluated with regard to the transmitted sound wave signal to determine at least the distance of each reflection site from the feed point.

16 Claims, 4 Drawing Sheets

(51) Int. Cl.
    *G01N 29/07*     (2006.01)
    *G01M 99/00*     (2011.01)
    *G01S 15/88*     (2006.01)
    *G01S 7/539*     (2006.01)
    *G01S 15/10*     (2006.01)

(52) U.S. Cl.
    CPC ............ *G01S 7/539* (2013.01); *G01S 15/104* (2013.01); *G01S 15/88* (2013.01); *G01N 2291/011* (2013.01); *G01N 2291/044* (2013.01)

(58) Field of Classification Search
    CPC .... G01N 2291/011; G01N 2291/02854; G01S 7/539; G01S 15/104; G01S 15/88
    USPC .................................. 73/579, 586, 592, 597
    See application file for complete search history.

(56) References Cited

U.S. PATENT DOCUMENTS

| | | | | |
|---|---|---|---|---|
| 6,751,560 | B1 * | 6/2004 | Tingley | ................. G01N 22/02 702/51 |
| 2011/0239781 | A1 * | 10/2011 | Petroff | .................... G01F 1/002 73/861.28 |
| 2014/0373631 | A1 * | 12/2014 | Davis | ................... G01B 17/025 73/627 |

FOREIGN PATENT DOCUMENTS

| | | | | |
|---|---|---|---|---|
| DE | 102008021727 | B4 | | 8/2012 |
| GB | 1302028 | A | * | 1/1973 ............ G01N 29/12 |
| JP | H0783646 | A | | 3/1995 |
| JP | H10132542 | A | | 5/1998 |
| JP | 2002196074 | A | | 7/2002 |
| WO | 8901130 | A1 | | 2/1989 |
| WO | 2010020817 | A1 | | 2/2010 |

OTHER PUBLICATIONS

Acoustic Waveguides, John Price, University of Colorado, Boulder, Jan. 22, 2008.

\* cited by examiner

METHOD AND APPARATUS FOR DETERMINING PROPERTIES OF A PIPELINE, IN PARTICULAR THE POSITION OF A BRANCH OF A SEWAGE PIPELINE

TECHNICAL FIELD OF THE INVENTION

The invention relates to a method for determining properties of a pipeline, in particular the position of a branch of a sewage pipeline, as well as to an apparatus suitable therefor.

BACKGROUND OF THE INVENTION

For the inspection, maintenance and renovation of duct systems, for example, sewage duct systems, controllable self-propelled robots are usually used, which are capable of performing the required measurement processes or mechanical renovation work. For this purpose, the robots usually have a camera system for visualizing the state of the duct. For example, if a sewage duct is not airtight at a certain location, then a tubular liner can be pulled in, which can be, for example, impregnated with epoxy resin and which therefore cures rapidly. If such liners are pulled in, then it is necessary to again open up duct branches, house connections and the like, which at first are closed by the tubular liner, after the curing. For this purpose, the exact position and size of the closed branch obviously have to be known. In order to determine the position of branches before closing with the tubular liner, the conventional approach is to measure the distance of a branch from a reference site using a mechanical length measurement device attached to the self-propelled robot. In the simplest case, this can be simply a kind of measuring tape.

Naturally, the most exact possible position determination is not required only in the case of the above described renovation case. In fact, for certain features within a duct or duct system, or very generally for any pipeline or any pipeline system, it is often desirable to determine the associated positions. In addition to the already mentioned branches, such features of interest can be bends, diameter changes or (annular) slits, for example.

However, the determination of the position associated with a certain feature of the duct system using a mechanical length measurement system is expensive and prone to error.

Therefore, the present invention is based on the problem of creating a method and an apparatus with which at least the position of a feature of interest of a pipeline or of a pipeline system can be determined reliably, rapidly and cost effectively with the simplest means possible.

SUMMARY OF THE INVENTION

The invention is based on the finding that a pipeline or a pipeline system can be examined in a simple manner to determine certain properties if a transmitted sound wave signal is fed into the pipeline and reflected signal portions are detected and evaluated as a received sound wave signal at the site of the feed. The evaluation here is performed while taking into consideration the transmitted sound wave signal with regard to the presence of reflection sites along the pipeline that cause sound wave reflections.

Here, it should be noted that, in the present description, the term "pipeline" is considered to be a synonym of both a pipeline of any design and also of a pipeline system that can consist of several individual pipelines and that can also comprise branches.

According to the invention, the transmitted sound wave signal has at least one frequency component or a spectral range whose maximum frequency is smaller than the lower limit frequency of the first upper mode capable of propagating in the pipeline. Indeed, spectral components of a transmitted or received sound wave signal that are in a frequency domain in which only the fundamental mode is capable of propagation have a speed of sound that is substantially equal to the speed of sound of a plane wave in free space (in a certain medium). The signal travel time can thus be used with sufficient accuracy for determining the corresponding distance. In the case of such a signal, dispersion effects play no role.

If the pipe diameter is known, it is possible, in addition, to calculate the speed of sound of the signal from the speed of sound of a plane wave and to use it for determining the distance from the measured signal travel time.

According to the invention, from the received sound wave signal, at least the distance of the reflection site from the feed point is determined.

According to an embodiment of the invention, one can use, as a transmitted sound wave signal, a sound pulse that either has a fixed (carrier) frequency or is configured as a chirp pulse, i.e., it has a frequency that increases from the pulse start to the pulse end, for example.

For the signal evaluation, it is suitable to use, for example, correlation methods that can achieve a high sensitivity. In particular, for reasons pertaining to the computational expenditure required, a transformation of the transmitted sound wave signal and all or part of the received sound wave signal to the complex domain can be performed, because here the calculation of the correlation function or of the convolution integral can occur simply by multiplication. After a (back) transformation of the correlation function into the time domain, the entire signal travel time consisting of the travel time of the transmitted sound wave signal from the feed site to the respective reflection site, and the travel time of the reflected partial signal from the respective reflection site back to the feed site, can be determined by the determination of the temporal position of the associated maximum of the correlation function in the time domain (more precisely: the value of the complex correlation function in the time domain).

As already explained above, the position of the reflection site can then be determined from this measured and calculated travel time and from the known speed of sound of a plane wave or of the calculated speed of sound of the fundamental mode in the pipeline in question.

According to an additional implementation of the method according to the invention, one or more reflected portions that can be temporally separated from the received sound wave signal are cut out at a predetermined time interval from the received sound wave signal and analyzed with regard to the time course and/or the frequency course of the amplitude and/or of the frequency course of the phase or with regard to the deviation of the time course and/or of the frequency course of the amplitude and/or the frequency course of the phase from the respective course of the transmitted sound wave signal after the appearance of predetermined features. Depending on the appearance of one or more predetermined features, the respective portion of the received sound wave signal can then be assigned to a general class of reflection sites. As classes, it is possible to define, for example, the classes of "pipeline branch," or "change in the pipeline diameter," or "bend of the pipeline," or "obstacle within the pipeline."

According to an embodiment of the invention, by means of the classification, it is possible to determine, in addition to the general class (i.e., the general type of the reflection site), from the one or more predetermined features, quantitative information for a reflection site, such as the diameter of a pipeline branch, the value of the absolute or relative increase or reduction of the diameter of the pipeline, the angle of the bend of the pipeline or the type and/or size of the obstacle within the pipeline.

Since the speed of sound within a medium depends on the density and thus also on the temperature of the medium, it is advantageous if the temperature of the medium (for example, air) within the pipeline is determined and used for the determination of the speed of sound (of a plane wave or of the actual speed of sound of the fundamental mode) in the respective medium. For this purpose, the temperature can be measured using a suitable conventional temperature sensor and it can be determined from a known dependency of the speed of sound (of a plane wave or of the fundamental mode) in the respective medium using the measured temperature.

However, the speed of sound of a plane wave or of the fundamental mode at the current temperature and in the presence of the given medium within the pipeline can also be determined directly using a sound wave measurement signal that has a frequency or frequency spectrum at which the sound wave measurement signal within the pipeline can be processed with sufficient accuracy as a plane sound wave, wherein, for this purpose, the travel times of the sound wave measurement signal is measured over a known distance in both directions.

The speed of sound thus determined for a plane wave at the current temperature within the pipeline (which, to simplify, is assumed to be constant within the pipeline) can then be equated with a very good approximation to the speed of sound of the fundamental mode at this temperature. Indeed, the speed of sound of the fundamental mode is independent of the diameter of the pipeline and it is influenced only to a relatively small extent by the surface constitution of the inner wall of the pipeline.

The speed of sound thus determined can then be used for the determination of the distance of a reflection site along the pipeline from the feed point in question.

Here, it is not necessary that the pipeline, for example, a sewage pipe or pipe system, has been completely emptied or rinsed clear. Indeed, the speed of sound of the fundamental mode is practically independent of the pipe diameter. The only condition that needs to be satisfied is that substantially only the fundamental mode is capable of propagation. Thus, in the case of a sewage pipeline system, it is not detrimental if water remains in some sections in the tube because the actually required gradient was not maintained or because a pipe section has sunk.

The speed of sound c can here be calculated according to the relationship $c = L/2 \cdot (t_2 + t_1)/(t_1 \cdot t_2)$, where $t_1$ denotes the measured travel time along the length L in the forward direction and $t_2$ denotes the measured travel time along the length L in the backward direction.

According to an additional embodiment of the invention, the known length for the measurement of the speed of sound c of a plane wave within the pipeline can extend parallel to the axis of the pipeline, preferably in or near the axis of the pipeline. This provides the possibility of also determining the speed v of the medium within the pipeline (for example, the wind speed within a sewage duct). Said speed can also be determined from the measured travel times $t_1$ and $t_2$ according to the relationship $v = L/2 \cdot (t_2 - t_1)/(t_1 \cdot t_2)$. The speed v can also be taken into consideration in the calculation of the position of a reflection site, wherein, for a distance $l_R$ of a reflection site from the feed point for the transmitted sound wave signal or from the detection point for the received sound wave signal, the relationship $l_R = t_g \cdot (c^2 - v^2)/(2 \cdot c)$ is obtained. Here, $t_g$ denotes the total travel time determined.

Therefore, the position of a reflection site can be determined with high accuracy, since the speed of sound of the transmitted sound wave signal (in the fundamental mode) can be corrected both with regard to the temperature and also with regard to the speed of the medium in the pipeline.

If a value for the speed of sound thus determined is obtained that indicates that the medium presumed to be in the pipe accordingly would have to have a temperature that obviously does not correspond to reality, then it can be concluded therefrom that the assumed medium, for example, air, is not present. This can be caused, in the case of sewage ducts, for example, by the presence of fermentation gases. In such a case, the measurement device according to the invention (in particular the control and evaluation unit) can generate an error signal or an error notice, which can consist, for example, of a "blow-out warning," i.e., the pipeline should be cleared by blowing out noxious gases with a blower. Thereafter, a known medium is then in the pipeline, so that the measurement method according to the invention can be used with high accuracy.

As explained above, the inner diameter of the pipeline can be used for the most exact possible determination of the speed of the fundamental mode. However, the diameter is also crucial for the lower limit frequency of the first upper mode. Thus, the frequency or the frequency spectrum of the transmitted sound wave signal can be selected depending on the diameter, for example, in such a way that the same transmission frequency normalized to the limit frequency, or the same transmission spectrum normalized to the limit frequency, is always obtained.

Moreover, the pipe diameter can also be used in order to receive a representation—normalized to the limit frequency of the first upper mode—of the received sound wave signal or of the frequency courses of signal portions of the reflected signal or of signal portions of the received sound wave signal correlated with the transmitted sound wave signal. In this manner, as explained above, a simple classification of reflection causes or reflection sites can be achieved. According to an embodiment of the invention, the inner diameter of the pipeline can be determined by distance measurements in at least three radial acquisition directions by means of sound signals. The sound signals are transmitted in each case from a site within the pipeline in the radial direction and reflected by the inner wall of the pipeline. In the process, the travel time between the transmission of the sound signal and the reception of an associated sound signal reflected on the inner wall of the pipeline is determined in each case. The travel time here can be determined directly by the transmission and reception of a pulse-like sound signal with very small pulse width and by the measurement of the time difference between the transmission and reception (possibly also using the above-explained correlation method). Alternatively, in each case, a sound signal can be transmitted that has a temporal length that is greater than the total travel time between the transmission of the sound signal and the reception of the reflected sound signal in question. Depending on the frequency of the signal, by means of a measurement of the phase shift between the transmitted signal and the received signal, the total travel time can be determined. If, for the distance measurement, a sound signal is used that has a small wavelength relative to the pipe diameter (less than 1/10 of the diameter, for example), then the evaluation of the phase produces a high accuracy at low cost in terms of measurement technology.

As sound transmitters and/or sound sensors, piezo ultrasound transducers can be used, for example, which can function both as a sound generators and also as sound sensors. Such piezo ultrasound generators/sensors are available at low cost and they can generate ultrasound at frequencies higher than 100 kHz.

Such ultrasound transmitters or ultrasound sensors usually have a wedge-shaped characteristic, which, for example, at an angle of ±30° with respect to the axis, still have a sensitivity decrease or radiation power decrease of less than 3 dB. The ultrasound transmitters or ultrasound sensors are oriented so that the axis of the radiation wedge extends perpendicularly with respect to the longitudinal axis of the pipeline. Since, even in the case of an off-center arrangement of an ultrasound transmitter (i.e., the axis of the wedge does not intersect with the longitudinal axis of the pipeline), the transmitted signal portions that contribute most to the received reflected signals are those transmitted along an axis that extends through the longitudinal axis of the pipeline (and perpendicularly thereto) and the (center) position of the ultrasound transmitter (other portions are reflected at a slant), the smallest distance between the respective ultrasound transmitter and the inner wall of the pipeline is thus measured in each case.

The pipe diameter can be determined from these triplets or n-tuplets of measured values in that, for each possible position of the measurement arrangement (with fixed positions of the pairs of sound transmitters and sensors) within a pipeline having a predetermined diameter, a reference triplet or n-tuplet is determined in each case. This results in a two-dimensional surface in a three-dimensional or n-dimensional vector space. Naturally, the surface can also be established by means of a selected number of support values. Other points on the surface can then be determined by an analytical description of the surface or by interpolation methods.

Since a separate surface is obtained for each pipe diameter, it is possible to determine the associated pipe diameter by a comparison of the measurement triplet or n-tuplet with a known, previously determined surface.

In practice, stepped or normalized inner diameters are often relevant. Thus, for house duct systems, pipes of 100 mm or 200 mm are conventionally used. This simplifies the determination of the inner diameter, because, instead of an exact diameter determination, all that needs to take place is an assignment to predetermined discrete diameter values. If, in such a case, the determination by measurement technology would give a diameter that differs from all the predetermined discrete values, then it is possible to use the closest discrete value as correct value, for example.

Here, it should be pointed out that the above-explained determination of the diameter of a pipeline can also be used separately from the determination of properties of the pipeline by the axial feeding of sound signals into the pipeline and the evaluation of reflected signal portions.

DESCRIPTION OF REPRESENTATIVE EMBODIMENTS

Figure 1:
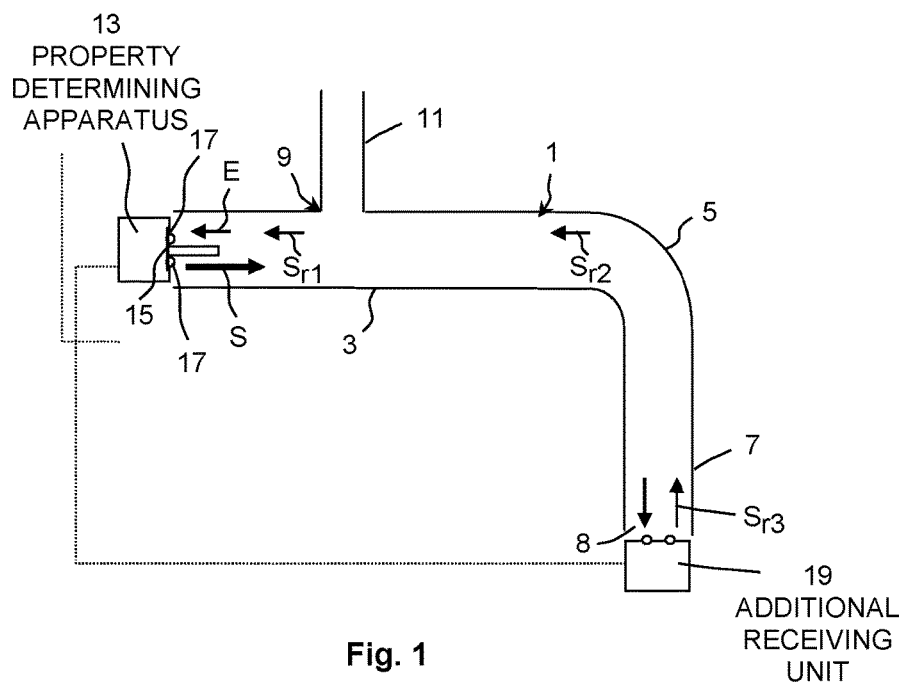
FIG. 1 a diagrammatic representation of a pipeline system with a branch and with a bend, and with an apparatus for determining properties of a pipeline according to the invention as an explanation of the method according to the invention, wherein the pipeline system is examined starting from one point of the pipeline system.

FIG. 1 shows a diagrammatic representation of a pipeline system 1 or a cutout of a more complex pipeline system, wherein the cutout shown in FIG. 1 comprises a first straight section 3, a curved section 5 that has a bend angle of 90°, and a second straight section 7. In the central section of the first straight section 3, a branch 9 is provided. The inner diameter D of the main pipeline with the straight sections 3, 7 and the curved section 5 has a diameter D that is greater than, for example, twice as large as, the inner diameter d of the branching pipeline 11. The end of the second straight section 7 of the main pipeline is open. Overall, the represented pipeline system 1 represented or the respective cutout can be, for example, a portion of a sewage pipeline system, for example, within a building or in a house connection area. Typical pipe diameters here are in the range from 100 mm to 400 mm.

Figure 3:
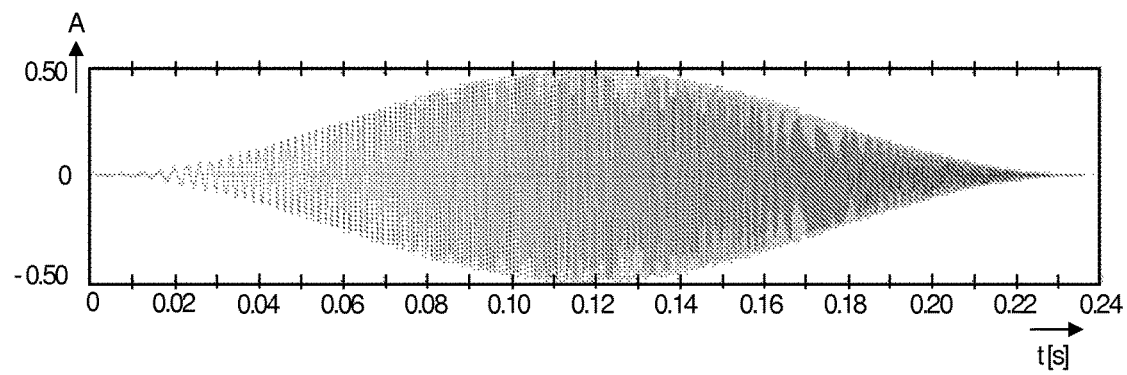
FIG. 3 a representation of a transmitted sound wave signal in the form of a chirp pulse (normalized amplitude of the sound pressure as a function of time)

In order to be able to determine certain properties of such a pipeline system 1 as simply, rapidly and cost effectively as possible, a transmitted sound wave signal S is fed into the pipeline system 1 for the determination of properties of the pipeline system. For this purpose, as shown in FIG. 1, the apparatus 13 is positioned in front of the opening of the pipeline, here the opening of the first straight section 3. In practice, the apparatus 13 can of course be introduced into the pipeline system at any accessible place of the pipeline system in such a manner that the transmitted sound wave signal S is fed into the pipeline system 1 substantially in the axis of the respective pipeline or the respective pipeline section. The apparatus 13 here must obviously have an appropriate size. As represented in FIG. 3, the transmitted sound wave signal can be configured as a temporally brief sound pulse of, for example, approximately 0.2 sec. Since certain properties of the pipeline system, with respect to attenuation or phase shift, act differently on different frequencies or spectral portions of the transmitted sound wave signal S, it is advantageous if the transmitted sound wave signal has not only a fixed carrier frequency, which is amplitude-modulated with respect to time, but also has an appropriate frequency spectrum. For this purpose, as shown in FIG. 3, a transmitted sound wave signal S can be configured in the form of a chirp pulse which, at the beginning, has a relatively low frequency, which increases linearly or exponentially toward the end of the pulse, for example. The envelope curve corresponding to the (normalized) amplitude A can also be selected in an appropriate form and it can be established by using a corresponding filter in the electrical signal path that is used for actuating the sound transducer.

The frequency or the frequency spectrum of the transmitted sound wave signal S is selected so that the single carrier frequency or the predominant portion of the frequency spectrum of a spectrally broader transmitted sound wave signal S, such as a chirp pulse according to FIG. 3, is below the lower limit frequency $f_c$ of the first upper mode that is capable of propagating in the pipeline. Since, usually, the transmitted sound wave signal S is fed into a main pipeline with a diameter that is constant over a longer span, the frequency or the frequency spectrum of the transmitted sound wave signal S can be adapted to this span of the pipeline system.

For example, if a pipe system is to be examined that has a predominant diameter of 200 mm, then one gets, for the lower limit frequency of the first upper mode, a value of $f_c=0.586 \cdot c/D \approx 1$ kHz, where D is the predominant diameter of the pipe and c is the speed of sound of a plane wave or of the fundamental mode within the pipe through a given medium. Accordingly, the chirp pulse shown in FIG. 3 in this case can have a frequency spectrum of approximately 50 Hz to 1 kHz.

If a pipeline system with smaller diameter D is to be examined, for example, a pipeline system having a diameter of D=100 mm, then an appropriate chirp pulse should be located at least with the predominating portion of its spectrum under the limit frequency of approximately 100 Hz to 2 kHz.

The apparatus 13 comprises, for the generation of the transmitted sound wave signal S, a sound transducer 15, for example, in the form of a speaker that converts an electrical driver signal having the desired properties into the desired transmitted sound wave signal S.

Since the transmitted sound wave signal S has a frequency or frequency spectrum that is exclusively or predominantly below the lower limit frequency $f_c$ of the first upper mode capable of propagating in the pipeline system 1, the power of the transmitted sound wave signal within the pipeline is conducted predominantly in the fundamental mode. Signal portions that excite upper modes at the time of feeding into the pipeline are so attenuated that they fade away already after a short distance.

Since the acoustic fundamental mode in the pipeline has nearly exactly the speed of sound in free space and is independent of the material of the pipe wall, the corresponding sound signal can be used in order to determine, on the basis of the signal travel time, a certain position within the pipeline with high accuracy. Indeed, the speed of sound c of the fundamental mode or of the plane wave is known with high accuracy as a function of the medium or of the composition of the medium and the temperature and the density of the medium. For example, the speed of sound c of a plane wave in air at a temperature of 20° C. is approximately 343 m/sec.

In order to measure the signal travel time in a pipeline or in a cutout of a pipeline system 1 reliably, it should be filled homogeneously with a medium, for example, with air. If, for example, a sewage pipeline system within a building or in a house connection area is to be examined, then the pipe capacity should be closed off and emptied to the extent possible. In this way, biasing of the measurement results due to pipeline areas that are partially filled with sewage can be avoided.

Figure 7:
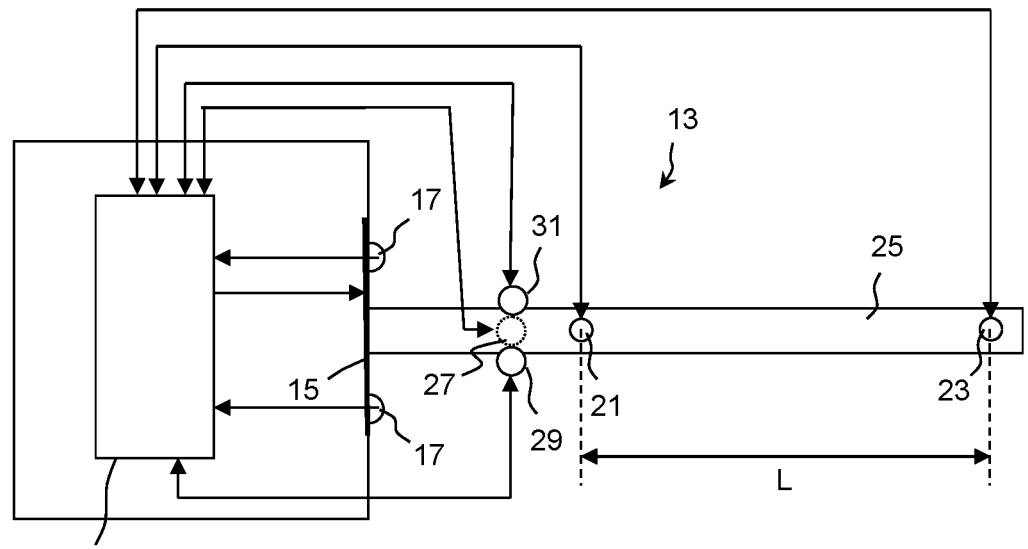
FIG. 7 a diagrammatic side view of an embodiment of an apparatus according to the invention for determining properties of a pipeline, which allows the acquisition of a sound wave signal reflected in a pipeline, as well as the measurement of the speed of sound and the speed of the medium in the pipeline and the measurement of the inner diameter of the pipeline, and FIG. 8 a diagrammatic front view of the apparatus according to FIG. 7.

As shown in FIG. 1, certain features within the pipeline system 1 cause reflections, so that reflected portions of the transmitted sound wave signal S are returned in the direction of the apparatus 13. In particular, the branch 9, the bend area 5, and the open end 8 of the second straight section 7 of the pipeline system 1 generate reflected signals designated $S_{r1}$, $S_{r2}$, $S_{r3}$. These signal portions are acquired at the feed site, that is at the site of the apparatus 13, by means of at least one sound transducer 17 (for example, in the form of a microphone), which is part of the apparatus 13. The sound transducers convert the detected received sound wave signal E, which is formed by the reflected signal portions $S_{r1}$, $S_{r2}$, $S_{r3}$ at the feed or reception site, into an electrical signal, which is then supplied to a control and evaluation unit 18 of the apparatus 13 (FIG. 7).

Here, it is noted that, for the generation of the transmitted sound wave signal S and for the reception of the reflected signal portions $Sr_1$, $S_{r2}$, $Sr_3$, it is obviously also possible to provide a more complex sound wave transmission unit—not shown—and a more complex sound wave receiving unit, which are part of the apparatus 13. The sound wave transmission unit here comprises the sound transducer or speaker 15 and a corresponding electronic control unit, for example, for generating an electrical chirp pulse that is converted by the sound transducer 15 into the acoustic chirp pulse. The sound wave transmission unit can be integrated (at least partially) into the control and evaluation unit 18.

The sound wave receiving unit comprises the at least one sound transducer 17, and it can additionally comprise a more complex signal processing unit, not shown, in particular an A/D converter unit, which samples the analog electrical signal, which is supplied by the at least one microphone 17, at a predetermined sampling rate and converts it into a digital signal that is then applied to the control and evaluation unit 18 for further processing. The sound wave receiving unit can also be integrated (at least partially, for example, excluding the sound transducers 17) in the control and evaluation unit 18.

The sampling rate for the acquisition of the reflected signal portions here must be selected so that the spectral portions of the received sound wave signal E formed by the reflected signal portions $Sr_1$, $S_{r2}$, $Sr_3$ are still acquired completely. For this purpose, the sampling theorem must be satisfied primarily; that is to say the sampling frequency for the received sound wave signal must be twice as large as the maximum frequency of the transmitted sound wave signal, or twice as large as the frequency of the received sound wave signal that is still to be resolved by the sound wave receiving unit. From the received sound wave signal E, the control and evaluation unit 18 can then determine, by means of an appropriate evaluation method, at least the distance to a reflection site that has caused the associated reflected signal portions $Sr_1$, $S_{r2}$ or $Sr_1$. For this purpose, the control and evaluation unit 18 can determine the total travel time $t_g$ consisting of the travel time $t_1$ of the transmitted sound wave signal S from the feed site to the respective reflection site and the travel time $t_2$ of the reflected signal portion from the reflection site back to the respective feed site or reception site. Using the speed of sound, which has to be corrected if necessary taking into consideration the pipe diameter and the temperature, the distance to the reflection site can then be calculated.

In addition, it is possible, as explained below, to determine not only the distance to a reflection site, but also the type and possibly additional features of the reflection site or of the reflection cause.

As diagrammatically shown in FIG. 1, it is naturally also possible to position an additional sound wave receiving unit 19 at the pipeline end, the received signal of which can then also be applied to the apparatus 13 or to the control and evaluation unit 18 thereof. This can occur either by wire connection or wirelessly. In this manner, the apparatus 13 or the control and evaluation unit 18 can determine in a simple way the length of the pipeline 1 between the feed site and the position of the additional sound wave receiving unit 19. The length is again obtained from the measured travel time between the transmitted sound wave signal S and the received signal detected by means of the sound wave receiving unit 19 and from the speed of sound c (again corrected by taking into consideration the pipe diameter and the temperature, if necessary).

In the same way, the transmitted signal can also be received by a sound wave receiving unit 19 that moves within the pipeline 1, wherein such a sound wave receiving unit is provided, for example, on a self-propelled robot. This sound wave receiving unit can also have an evaluation unit that determines, from an electrical signal supplied to it by wire connection or wirelessly, and from the detected sound signal, the travel time of the acoustic signal, and from this, the current position of the sound wave receiving unit within the pipeline 1. This evaluation can occur exactly as described above and also below, wherein obviously only one signal distance (from the feed site to the current position of the sound wave receiving unit) needs to be taken into consideration.

Figure 2:
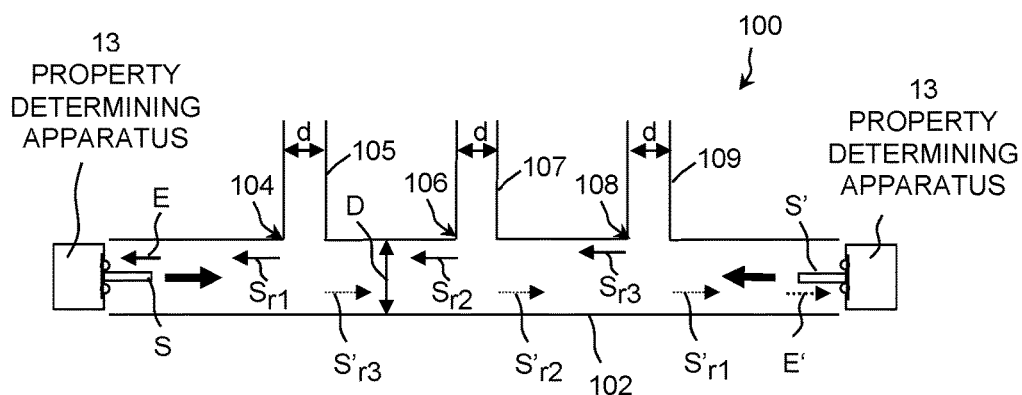
FIG. 2 a diagrammatic representation of an additional pipeline system with three branches as an explanation of the method according to the invention for determining the properties of a pipeline, where the pipeline system is examined from mutually facing points.

FIG. 2 shows an arrangement similar to that of FIG. 1, wherein the pipeline system 100 in this case has only one straight main line 102, from which three branches 104, 106, 108 branch off. The diameter of the main line 102 is again marked D. The diameters of the branching lines 105, 107, 109 of the branches 104, 106, 108 are marked d. In the represented example, the diameter d is approximately half of the diameter D of the main line 102.

As shown in FIG. 2, by means of one or two different apparatuses 13, the pipeline system 100 can be examined from both sides. The apparatus 13 shown in FIG. 2 on the left feeds the transmitted sound wave signal S, at the feed position at the left pipeline end, into the pipeline system 100. The branches 104, 106, 108 generate the reflected signal portions $Sr_1$, $S_{r2}$, $S_{r3}$. The latter signal portions are detected by apparatus 13 represented in FIG. 2 on the left, at the feed position, as transmitted sound wave signal E.

In the same manner, the apparatus 13, represented in FIG. 2 on the right, feeds the transmitted sound wave signal S', at the feed position at the right pipeline end, into the pipeline system 100. The branches 104, 106, 108 generate the reflected signal portions $S'_{r3}$, $S'_{r2}$ and $S'_{r1}$. Said signal portions are detected by apparatus 13 represented in FIG. 2 on the left, at the feed position, as received sound wave signal E.

The two measurements by means of the two apparatuses or the single apparatus 13 obviously occur temporally successively in order to prevent them from influencing each other. The measurement and evaluation occur in the same way as described before in connection with the embodiment according to FIG. 1. However, at slightly higher cost, it is also possible to implement a simultaneous measurement, for example, by using orthogonally modulated transmitted signals that can then be separated from one another at the time of detection. Measurement from both sides has the advantage that reflection sites located farther from the respective feed site can be acquired with higher accuracy, if the two measurement results are "superposed one on the other," for which purpose one of the measurement results or evaluation results obviously has to be "mirrored" (that is to say that in that case, for example, for a "mirroring of the received sound wave signal, E': $E'(t_{lg}-t_g)=E(t_g)$, where $t_{lg}$ refers to the total signal travel time, there and back over the total length $l_g$ of the main line 102). As an indication showing that the signal travel time $t_g$ is correct, the exact mutual fit the evaluated reflection signal from one side and the evaluated and mirrored reflection signal from the other side can be used.

Below, the method for evaluating the received sound wave signal, which includes the reflected signal portions, is explained in greater detail.

Figure 4:
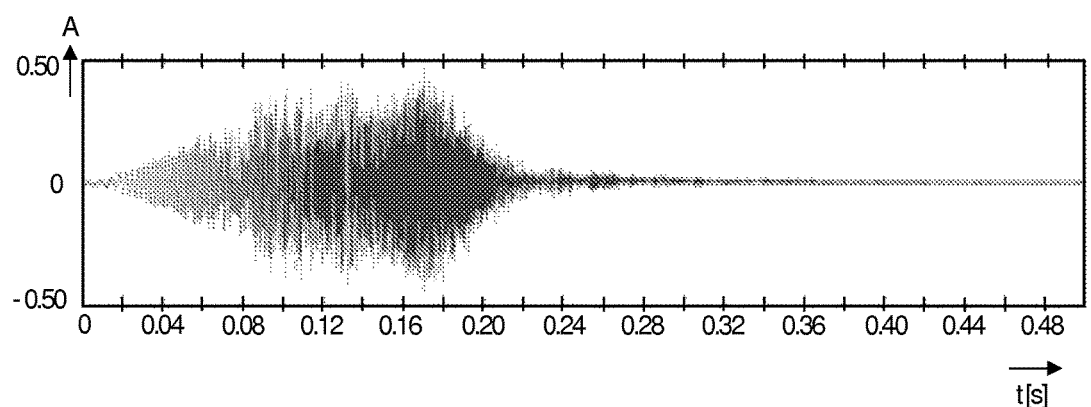
FIG. 4 a representation of a detected received sound wave signal (normalized amplitude of the sound pressure as a function of time), which is obtained in the case of a pipeline system that is not represented in further detail, using the chirp pulse according to FIG. 3.

As already explained above, by means of the apparatus 13, a transmitted sound wave signal S, as represented, for example, in FIG. 3 in the form of a chirp pulse, is fed at a feed position into the respective pipeline system 1, 100. The received sound wave signal E generated by the reflected signal portions $Sr_1$, $S_{r2}$, $Sr_1$ or $S'_{r1}$, $S'_{r2}$, $S'_{r3}$ is received and evaluated at the feed site, which at the same time is the detection site, by the apparatus 13. The sound wave receiving unit included in the apparatus 13 here comprises at least one sound transducer or microphone 17, for generating a received electrical signal, which is subsequently subjected to analog/digital conversion. FIG. 4 shows an example of such a received sound wave signal E.

Instead of a single sound transducer 17, several sound transducers can also be provided (for example, two sound transducers as shown in FIGS. 1 and 2), which are arranged so that they lie in a cross section plane, in which the sound pressure field of the first or higher upper modes have different signs. Due to the superposition with correct signs of the respective (electrical) received sound wave signals, the reception of higher modes, which are possibly excited at the reflection sites and returned in the form of reflected signal portions to the detection site, can then be suppressed. In this way, the influence of the dispersion (the upper modes no longer have the speed of sound of the fundamental mode) is avoided in the determination of the signal travel times and the reflected portions and thus in the determination of the distance of the respective reflection site from the feed site.

As explained above, the electrical received sound wave signal thus determined (see FIG. 4) is correlated with the (electrical) transmitted sound wave signal, i.e., the cross correlation function is calculated. Obviously, it is possible, for this purpose, for the (electrical) transmitted sound wave signal S or the electrical control signal for the sound wave signal transmitting unit with the sound transducer 15 and the received sound wave signal E to be in digital form.

The calculation of the correlation can be done either in the time domain or by the transformation of the (electrical) transmitted sound wave signal with the (electrical) received sound wave signal into the frequency domain and the corresponding back transformation. The fundamental principles of such signal processing are known and therefore do not have to be further explained here. In the calculation, it is also possible to take into consideration the entire transfer function of units located in the signal path, in particular the (partial) transfer functions of the sound transducer and the respective electrical control units and possibly electrical filtering units.

Figure 5:
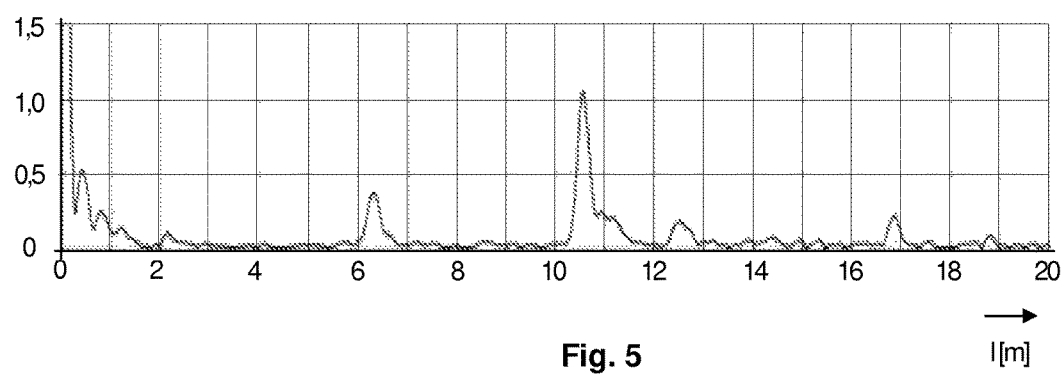
FIG. 5 a representation of the value of the correlation function (normalized amplitude as a function of the distance from the feed point or reception point) from the transmitted sound wave signal according to FIG. 3 and from the received sound wave signal according to FIG. 4.

FIG. 5 shows the results of such a correlation, wherein the represented curve is the value of the correlation function that has been back transformed into the time domain (the back transformed correlation function can also be a complex function in the time domain). The value of the temporal correlation function is here already plotted as a function of the distance from the feed or detection site. The distance can here be determined from the signal travel time by using a possibly corrected speed of sound. The back transformation can be carried out using known methods, for example, Wiener deconvolution.

The curve of the value of the correlated signal (more precisely, the complex correlation function back transformed into the time domain), which is represented in FIG. 5, shows, in the beginning range (up to approximately 2.5 m), a signal portion (a reflection peak) that is produced by reflection at the time of the feeding of the transmitted sound wave signal S into the pipeline system. This signal portion can be neglected in the signal evaluation. However, in addition, the curve in FIG. 5 also shows the reflected signal portions in the vicinity of approximately 6.3 m, in the vicinity of approximately 10.6 m, in the vicinity of approximately 12.5 m, in the vicinity of approximately 16.9 m, and in the vicinity of approximately 18.8 m.

The signal in FIG. 5 is a measurement result on an actual pipeline system that is not shown in further detail, and not an evaluated transmitted sound wave signal in the case of the pipeline systems 1, 100 represented in FIGS. 1 and 2.

For each reflection peak represented in FIG. 5, by determining the maximum of the reflection peak, the distance of the associated reflection site, for example, of a branch or of a diameter change of the respective pipeline, from the feed site can be determined.

In addition to the determination of the distance of a reflection site from the feed or detection site, a conclusion can also be drawn from the correlated signal regarding the type of the irregularity site at the respective reflection site. For this purpose, the respective reflection peak can be cut out from the correlated signal (in the time domain or as a function of the site, if the acquired travel time was converted with the (corrected) speed of sound into a site or into a distance from the feed site) with a sufficient width in order to acquire all the relevant signal portions that were caused by the reflection site in question. From the shape of the reflection peak of the correlated (time- or site-dependent) signal, one can then attempt to determine, by means of a comparison with pattern signals determined empirically or theoretically beforehand, the type of the irregularity site and possibly additional quantitative features of the irregularity site in question.

However, the sensitivity of the correlated signal in the time domain with respect to different reflection causes is still relatively low. Therefore, the cut out reflection peak is transformed into the frequency domain, and the spectral course of the amplitude and/or of the phase (or of the real and/or imaginary part of the transformed reflection peak) is compared to pattern courses patterns appropriately determined empirically or theoretically beforehand.

Figure 6:
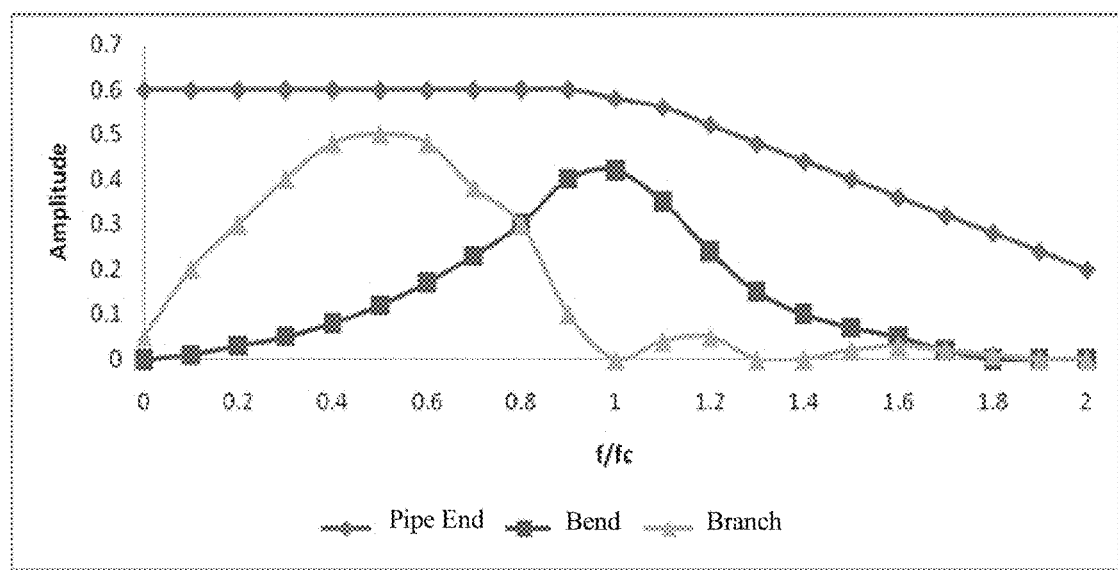
FIG. 6 different courses, as examples of spectra (amplitude as a function of the normalized frequency $f/f_c$; $f_c$ is the lower limit frequency of first upper mode) of cutouts from a correlated signal similar to FIG. 5.

As an example, for different amplitude spectra of different corresponding reflection peaks, FIG. 6 shows examples, for an open pipeline end, of reflected signal portions generated on a pipe bend or on a bend section and on a branch, which in each case have a clearly different course.

For a better comparison, the amplitude spectra of (cut out) reflection peaks determined from the acquired signal can be frequency normalized and also amplitude normalized. From the shape of the spectral course of the amplitude of the curves in FIG. 6, it is possible to draw a conclusion regarding the type of irregularity by a corresponding comparison with known pattern courses.

For the comparison of the curve courses determined from the received signal to the known curve courses, it is again possible to use a correlation method, for example.

By means of an evaluation of the absolute signal amplitude (in the time or frequency domain), it is possible, for example, to determine the reflection factor. From this, one can attempt to determine one or more quantitative features of the reflection cause, for example, the diameter of the branching pipe, the amount of change in diameter, the bend angle, etc.

An additional possibility consists of carrying out a classification of the data, determined by measurement technology and processed by computation, using neuronal networks. This type of data classification is known, so that no detailed explanations are required on this subject here.

Since both for an as exact as possible determination of the distance of a reflection peak from the feed or from the detection site, the speed of sound has to be known with sufficient accuracy, and the speed of sound depends in particular on the temperature within the pipeline, in FIG. 7, an additional detailed embodiment of an apparatus 13 for determining properties of a pipeline is represented, which, in addition has a device for determining the speed of sound or the temperature of the medium within the pipeline. The device for measuring the speed of sound comprises two sound wave transmission and receiving units 21, 23, which are arranged at a predetermined distance L. Each one of the sound wave transmission and receiving units 21, 23 can comprise a single sound transducer that can be operated either as a sound generator or as a sound sensor. Moreover, it is obviously also possible in each case to use one sound transducer that works as a sound transmitter and a second sound transducer that works as sound sensor.

The sound wave transmission and receiving units 21 can also be controlled by the control and evaluation unit 18 of the apparatus 13, or they deliver the detected electrical signals to the control and evaluation unit which then performs the other required evaluations.

For the measurement of the speed of sound, the control and evaluation unit 18 can first control the sound wave transmission and receiving unit 21 so that a transmitted sound wave signal is generated, which is transmitted in the direction of the sound wave transmission and receiving unit 23. The sound wave transmission and receiving unit 23 receives the sound signal and converts it into an electrical signal. The electrical signal is supplied to the control and evaluation unit 18 of the apparatus 13.

The control and evaluation unit 18 can then determine the signal travel time via the known length L by an evaluation of the phases of the transmitted signal and of the received signal, or directly by measuring the travel time of a pulse (for example, by measuring the time difference of the respective front flanks of a sound pulse).

For the measurement of the speed of sound, it is preferable to use a sound signal in the ultrasound range, since the generated sound field can be described satisfactorily by a plane wave. The speed of sound of a plane wave within the pipeline is thus determined (in other words: the wavelength of the transmitted sound wave signal used for the measurement of the speed of sound must be small compared to the inner diameter of the pipeline, in order to prevent the influence of the pipeline on the speed of sound; it is preferable for the wavelength to be smaller than one fifth of the inner diameter, and even better for it to be smaller than one tenth of the pipe diameter).

In the same way, the control and evaluation unit 18 can control the sound wave transmission and receiving units 23 and 21 or perform the evaluation in such a manner that the travel time of a signal generated by the sound wave transmission and receiving unit 23 and of a signal detected by the sound wave transmission and receiving unit 21 is acquired, and from this, the speed of sound is determined.

Due to the acquisition of the travel time $t_1$ in the direction of the sound wave transmission and receiving unit 23 and also of the travel time $t_2$ of a signal in the direction of the sound wave transmission and receiving unit 21, the possibility arises of measuring therefrom not only the speed of sound c at the given temperature within a pipeline, but also the speed of the medium, for example, of air, within the pipeline.

The speed of sound here is determined using the relationship $c=L/2\cdot(t_1+t_2)/(t_1\cdot t_2)$. The speed v of the medium within the pipeline is obtained using the relationship $v=l/2\cdot(t_2-t_1)/(t_1\cdot t_2)$.

The speed of sound c so determined at the given temperature can then be used directly by the control and evaluation unit for converting the acquired total travel time (travel time of the transmitted sound wave signal from the reflection site to the feed site or detection site) to a distance $I_R$ from the feed and detection site. For this purpose, there is relationship $I_R=I_g\cdot(c^2-v^2)(2\cdot c)$, where $t_g$ denotes the total travel time, that is the travel time of the transmitted sound wave signal to the reflection site, and the travel time of the reflected signal portion in the received signal E to the feed site.

Since, as explained above, to the extent possible, the temperature-independent speed of sound of a plane wave within the pipeline and also the speed of the medium (for example, the wind speed) within the pipeline are to be acquired, the sound wave transmission and receiving units 21, 23 are arranged on an arm 25 that is provided on the front side of the apparatus 13. As a result, at least the arm 25 with the sound wave transmission and receiving units 21, 23 can be introduced sufficiently far into the pipeline in question.

Figure 8:
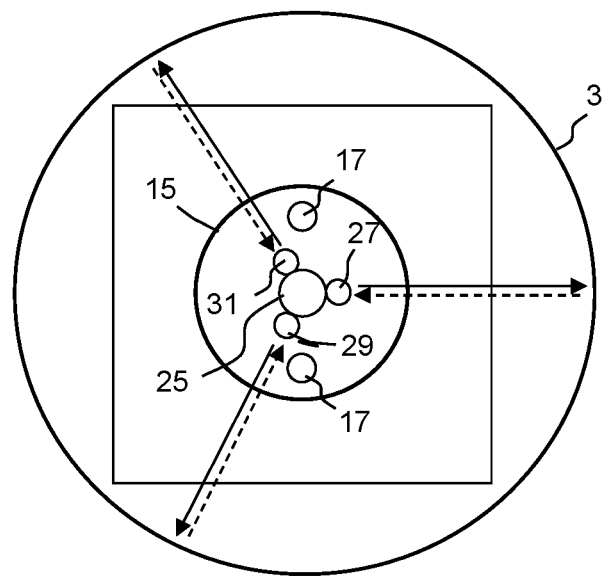

Below, an apparatus and a method for determining the inner diameter D of a pipeline 3 (FIG. 8) are described, wherein, for this purpose, an ultrasound measurement device is also used. FIGS. 7 and 8 show an apparatus 13 with three additional sound wave transmission and receiving units 27, 29, 31, which are arranged along the circumference of the arm 25 at an angular distance of approximately 120°. However, this arrangement is optional within broad limits.

In the axial direction, the sound wave transmission and receiving units 27, 29, 31 are arranged on the arm 25 so that they can be introduced sufficiently far into the pipeline in question, in order to determine, in each case by means of a radially transmitted sound wave signal, the distance of the respective sound wave transmission and receiving unit from the pipe inner wall.

The sound wave transmission and receiving units 27, 29, 31 can be configured exactly like the sound wave transmission and receiving units 21, 23, so that reference can be made to the above explanations.

The distance measurement occurs likewise by means of sound signals that are preferably in the ultrasound range in order to ensure sufficient resolution. Each one of the sound wave transmission and receiving units 27, 29, 31 can generate (in each case temporally one after the other) a transmitted sound wave signal that is transmitted in the radial direction. The signal reflected by the pipe inner wall is detected by the respective sound wave transmission and receiving unit. Due to the relatively small distances to be measured, it is possible, for the determination of the signal travel time, to measure the phase difference between the transmitted sound wave signal and the reflected signal and to determine the travel time from the known (constant) signal frequency in the ultrasound range. Since the transmission of the transmitted sound wave signal and the detection of the received signal must occur at the same time in this case, the sound wave transmission and receiving units 27, 29, 31 preferably each have two sound transducers, wherein one of the sound transducers operates as a sound generator and the other sound transducer as a sound sensor.

Using the previously measured speed of sound at the given temperature, the distance of the respective sound wave transmission and receiving unit 27, 29, 31 from the pipe inner wall can be determined with high accuracy.

If the arm 25 can be positioned with sufficient accuracy coaxially in the pipe or pipe section 3, then it is possible to determine the pipe diameter D from each one of the particular distances of the pipe inner wall from the respective sound wave transmission and receiving unit 27, 29, 31 and from the known distance of the respective sound wave transmission and receiving unit 27, 29, 31 from the axis of the arm 25 (or the axis of the pipe 3). By averaging the three pipe diameters determined in this way, an improvement of the accuracy can be achieved. However, as explained above, this is true only with a sufficiently accurate coaxial positioning of the arm 25 relative to the sound wave transmission and receiving units 27, 29, 31 within the pipe 3.

However, the pipe diameter can also be determined with sufficient accuracy if the arm 25 and the respective sound wave transmission and receiving units 27, 29, 31 are positioned as desired off-center in the pipe 3. In that case, in each case, triplets of distances of the respective sound wave transmission and receiving unit 27, 29, 31 from the inner wall of the pipe 3 are determined. These triplets of measured values can be thought of as three-dimensional vectors.

Since, for a certain pipe diameter, all the possible positions of the sound wave transmission and receiving units 27, 29, 31 form a two-dimensional surface in the three-dimensional vector space of the possible distances, and since such a distinct surface exists for each pipe diameter, it is possible to assign a distance triplet determined by measurement to a surface. Here, it is possible to show that the surfaces for the different pipe diameters do not intersect and accordingly an unequivocal assignment is possible.

In this manner, the control and evaluation unit 18, for the determination of the pipeline diameter, can first actuate the sound wave transmission and receiving unit 27, 29, 31 so that the individual distances and thus a measured value triplet are determined. The distance triplet so determined can then be assigned to a certain surface, as a result of which the pipe diameter associated with the respective surface is determined. For the description of the two-dimensional surfaces in the three-dimensional vector space, either analytical dependencies can be known for control and evaluation unit 18, or support points for each surface can be stored, wherein intermediate values of the surface can be determined by (nonlinear) interpolation. If the measured values are such that no sufficiently exact and unequivocal assignment to a two-dimensional surface can be determined, then an assignment to the surface that is closest can occur, for example, by determining a maximum probability.

This method can obviously also be implemented by using more than three sound wave transmission and receiving units. Here, one gets, instead of triplets, n-tuplets or two-dimensional surfaces in an n-dimensional vector space. The distance determination then occurs analogously.

In this connection, it is pointed out that the ultrasound generators or ultrasound sensors available in practice have a relatively broad wedge-shaped radiation or sensitivity characteristic, exhibiting a 3 dB drop only at an opening angle of ±30°. In the case of an off-center positioning of the sound wave transmission and receiving units 27, 29, 31, the shortest distance from the pipe inner wall is thus always determined, since the area of the surface of the inner wall of the pipe 3 that contributes the most to the reflection extends perpendicularly to the movement direction of the wave front (assuming a substantially overlapping characteristic of the sound generator and of the sound sensor).

Since such sound generators or sound sensors in the ultrasound range up to frequency ranges above 100 kHz are available extremely inexpensively, the pipe diameter can be determined simply, rapidly and highly accurately in this way. The computing power required for this purpose is already available in the control and evaluation unit 18 of the apparatus 13. Here, it is mentioned that the control and evaluation unit 18 obviously can be included in the housing of the apparatus 13, which is positioned in the pipe or in front of the pipe opening, or it can also be in a separate housing, wherein, in this case, the required signal transmission between the two apparatus portions can occur either by wire transmission or wireless transmission. Thus, it is possible, for example, to implement the control and evaluation unit 18 in a separate housing, for example, in the form of a PC or process computer that is connected by wire to the measurement unit itself, which is introduced into the pipeline or positioned in front of the pipe opening in question.

In summary, it can thus be noted that, by means of the above described method or the above described apparatuses, it is possible to make a simple, rapid and exact determination of at least the distance to irregularities of a pipeline and reflection sites formed thereby. By measuring the temperature-dependent speed of sound and the speed of the medium in the pipe interior, the accuracy is further improved. By the additional determination of the inner diameter of the pipeline in the feed area, it is possible, on the one hand, to achieve an even higher accuracy of the determination of the speed of sound of the fundamental mode and, on the other hand, the diameter can be used for calculating the lower limit frequency of the first upper mode. This limit frequency can be used for normalizing the spectral courses (amplitude course and/or phase course) of reflected signal portions, as a result of which a comparison with known patterns and a classification of the reflection causes becomes possible in a simple manner.

Moreover, from the amplitude of the determined reflected signal portions in the time domain and from the courses of the amplitude and/or of the frequency in the frequency domain normalized to the limit frequency, a conclusion can be drawn not only as to the type of irregularity (branch, bend, change in pipe diameter), but quantitative statements regarding certain properties of the irregularity can also be made. For example, from these data, using certain characteristic values or signal courses determined empirically or theoretically beforehand, a conclusion can be drawn regarding the diameter of a branching pipe, the extent of a change in diameter, or the angle of a bend.

LIST OF REFERENCE NUMERALS

1 Pipeline system
3 First straight section
5 Curved section
7 Second straight section
8 Open end of section 7
9 Branch
11 Branching pipe
13 Apparatus for determining properties of a pipeline
15 Sound transducer, speaker
17 Sound transducer, microphone
18 Control and evaluation unit
19 Sound wave receiving unit
21 Sound wave transmitting and receiving unit
23 Sound wave transmitting and receiving unit
25 Arm
27 Sound wave transmitting and receiving unit
29 Sound wave transmitting and receiving unit
31 Sound wave transmitting and receiving unit
100 Pipeline system
102 Main line
104 Branch
105 Branching line
106 Branch
107 Branching line
108 Branch
109 Branching line
D Inner diameter of the main pipeline
d Inner diameter of the branching pipeline 11
S, S' Transmitted sound wave signal
$S_{r1}$; $S'_{r1}$ Reflected signal portion
$S_{r2}$; $S'_{r2}$ Reflected signal portion
$S_{r1}$; $S'_{r3}$ Reflected signal portion
E, E' Received sound wave signal
L Known section for determining the speed of sound
I Distance from the feed and detection site

The invention claimed is:

1. A method for determining properties of a pipeline, the method including:
    (a) feeding a transmitted sound wave signal at a feed point into the pipeline so that the transmitted sound wave signal propagates in a longitudinal axial direction of the pipeline, the frequency spectrum of the transmitted sound wave signal having a frequency component or a spectral range with a maximum frequency that is less than a lower limit frequency for a first upper mode capable of propagating in the pipeline;
    (b) detecting a received sound wave signal, the received sound wave signal including, for each sound wave reflection site along the pipeline, a respective reflected portion of the transmitted sound wave signal reflected within the pipeline at that sound wave reflection site;
    (c) feeding a velocity measurement sound wave signal into the pipeline in both directions over a known length within the pipeline, receiving the velocity measurement sound wave signal, measuring a respective travel time of the velocity measurement sound wave signal in both directions over the known length within the pipeline, and determining an observed speed of sound within the pipeline; and
    (d) while taking the observed speed of sound as an actual speed of sound of a fundamental mode at conditions within the pipeline, determining at least a distance of each sound wave reflection site from the feed point by evaluating the received sound wave signal with respect to the transmitted sound wave signal.

2. The method of claim 1 wherein the transmitted sound wave signal is a chirp pulse whose highest frequency is below the lower limit frequency for the first upper mode capable of propagating in the pipeline.

3. The method of claim 2 wherein evaluating the received sound wave signal includes establishing a correlation of the received sound wave signal with the transmitted sound wave signal.

4. The method of claim 3 wherein the correlation of the received sound wave signal with the transmitted sound wave signal is established by a transformation of the transmitted sound wave signal and the received sound wave signal into a complex frequency domain and by calculating a correlation in a complex domain, and wherein the correlation of the received sound wave signal with the transmitted sound wave signal includes determining changes of both the amplitude and also of the phase of the received sound wave signal in comparison to the transmitted sound wave signal.

5. The method of claim 3 further including:
(a) cutting out from the received sound wave signal a respective reflected portion that is temporally separable from the received sound wave signal;
(b) for a respective reflected portion that is temporally separable from the received sound wave signal, analyzing the respective reflected portion with respect to a time course or a frequency course of the amplitude, or a frequency course of the phase, or with respect to the deviation of the time course or the frequency course of the amplitude or the frequency course of the phase from a corresponding course of the transmitted sound wave signal; and
(c) assigning the respective reflected portion to one of a number of different classes of reflection sites in the event the respective reflected portion exhibits one or more predetermined features, the number of different classes of reflection sites including a pipeline branch, a change in the pipeline diameter, a bend of the pipeline, and an obstacle within the pipeline.

6. The method of claim 5 further including determining quantitative information for the respective sound wave reflection site from one or more predetermined features of the respective reflected portion, the quantitative information comprising at least one of pipeline branch diameter, a value of absolute or relative increase or reduction of pipeline diameter, angle of bend in the pipeline, or a type or size of an obstacle within the pipeline.

7. The method of claim 1 wherein the speed of sound along the known length is determined according to the relationship $c=L/2\cdot(t_2+t_1)/(t_1\cdot t_2)$, where L denotes the value of the length, $t_1$ denotes the travel time measured along the length (L) in a forward direction, and $t_2$ denotes the travel time measured along the length (L) in a back direction.

8. The method of claim 7 wherein the known length extends parallel to the longitudinal axis of the pipeline and further including determining the speed of a medium in the pipeline according to the relationship $v=L/2\cdot(t_2-t_1)/(t_1\cdot t_2)$, and wherein the distance of a respective sound reflection site from the feed point is determined by the relationship $l_R=t_g\cdot(c^2-v^2)/(2\cdot c)$, where $t_g$ denotes total travel time of the sound wave signal from the feed point to the reflection site and of a portion of the received sound wave signal reflected there back to the location of the feed point along the length of the pipeline.

9. The method of claim 1 further including:
(a) transmitting a respective diameter measurement sound signal from each of at least three transmission sites at a location along the length of the pipeline, each diameter measurement sound signal having a wavelength that is less than 1/10 of the diameter of the pipeline, being transmitted from the respective transmission site in a respective radial acquisition direction, and being reflected at the inner wall of the pipeline back for detection at the respective transmission site; and
(b) determining an inner diameter of the pipeline based on a speed of sound within the pipeline, the travel time of each respective diameter measurement sound signal from the respective transmission site to the inner wall of the pipeline and back to the respective transmission site, and the distances between the at least three transmission sites.

10. The method of claim 5 further including determining a temperature within the pipeline and normalizing frequency in a frequency course based on the temperature within the pipeline or determining a pipeline inner diameter and normalizing frequency in the frequency course based on the pipeline inner diameter.

11. An apparatus for determining properties of a pipeline, the apparatus including:
(a) a sound wave transmission unit for feeding a transmitted sound wave signal into the pipeline from a feed point, the frequency spectrum of the transmitted sound wave signal having a frequency component or a spectral range with a maximum frequency that is less than a lower limit frequency of a first upper mode capable of propagating in the pipeline;
(b) a sound wave receiving unit for detecting a received sound wave signal, the received sound wave signal including, for each sound wave reflection site along the pipeline, a respective reflected portion of the transmitted sound wave signal reflected within the pipeline at that sound wave reflection site;
(c) a measurement device including two sound wave transmission and receiving units separated by a predetermined distance and being operable for feeding a velocity measurement sound wave signal into the pipeline in both directions between the two sound wave transmission and receiving units; and
(d) a control and evaluation unit operably connected to the measurement device, the sound wave transmission unit, and the sound wave receiving unit, and being operable to (i) determine an observed speed of sound within the pipeline based on travel time of the velocity measurement sound wave signal between the two sound wave transmission and receiving units, to (ii) control the sound wave transmission unit, and to (iii), taking the observed speed of sound as an actual speed of sound of a fundamental mode at conditions within the pipeline, determine at least a distance of each sound wave reflection site from the feed point by evaluating the received sound wave signal with respect to the transmitted sound wave signal.

12. The apparatus of claim 11 wherein the transmitted sound wave signal is a chirp pulse whose highest frequency is below the lower limit frequency of the first upper mode capable of propagating in the pipeline.

13. The apparatus of claim 12 wherein evaluating the received sound wave signal includes establishing a correlation of the received sound wave signal with the transmitted sound wave signal.

14. The apparatus of claim 13 wherein the correlation of the received sound wave signal with the transmitted sound wave signal is established by a transformation of the transmitted sound wave signal and the received sound wave signal into a complex frequency domain and by calculating a correlation in a complex domain, and wherein the correlation of the received sound wave signal with the transmitted sound wave signal includes determining changes of both the amplitude and also of the phase of the received sound wave signal in comparison to the transmitted sound wave signal.

15. The apparatus of claim 11 wherein the two sound wave transmission and receiving units are mounted on an elongated arm that is connected at a first end to the sound wave transmission unit and to the sound wave receiving unit.

16. The apparatus of claim 11 further including a diameter measuring arrangement including three sound wave transmission and reception devices which are each operably connected to the control and evaluation unit and which are each arranged for transmitting a respective diameter measurement sound signal in a respective radial acquisition direction, and wherein the control and evaluation unit is further operable to determine an inner diameter of the pipeline based on a speed of sound within the pipeline, the travel time of each respective diameter measurement sound signal from the respective sound wave transmission and reception device to the inner wall of the pipeline and back to the respective sound wave transmission and reception device, and the distances between the three sound wave transmission and reception devices.

\* \* \* \* \*